(12) United States Patent
Hartoumbekis et al.

(10) Patent No.: US 9,968,344 B2
(45) Date of Patent: May 15, 2018

(54) SURGICAL INSTRUMENT WITH ADAPTER FOR FACILITATING MULTI-DIRECTION END EFFECTOR ARTICULATION

(71) Applicant: Covidien LP, Mansfield, MA (US)

(72) Inventors: Elias Hartoumbekis, New Haven, CT (US); Roddi Simpson, Higganum, CT (US); Earl Zergiebel, Guilford, CT (US)

(73) Assignee: Covidien LP, Mansfield, MA (US)

( * ) Notice: Subject to any disclaimer, the term of this patent is extended or adjusted under 35 U.S.C. 154(b) by 0 days. days.

(21) Appl. No.: 15/202,045

(22) Filed: Jul. 5, 2016

(65) Prior Publication Data

US 2016/0310119 A1     Oct. 27, 2016

Related U.S. Application Data

(63) Continuation of application No. 13/479,654, filed on May 24, 2012, now Pat. No. 9,381,010.

(60) Provisional application No. 61/501,478, filed on Jun. 27, 2011.

(51) Int. Cl.

| A61B 17/00 | (2006.01) |
|---|---|
| A61B 17/02 | (2006.01) |
| A61B 34/00 | (2016.01) |
| A61B 17/29 | (2006.01) |
| A61B 34/30 | (2016.01) |

(52) U.S. Cl.
CPC .... *A61B 17/00234* (2013.01); *A61B 17/0218* (2013.01); *A61B 34/70* (2016.02); *A61B 34/71* (2016.02); *A61B 2017/00323* (2013.01); *A61B 2017/00327* (2013.01); *A61B 2017/291* (2013.01); *A61B 2034/302* (2016.02)

(58) Field of Classification Search
CPC ................ A61B 17/0218; A61B 19/22; A61B 2019/2215; A61B 2017/00323; A61B 2017/291; A61B 2019/2242; A61B 17/00234; A61B 34/70; A61B 34/71; A61B 2034/302; A61B 17/00327
See application file for complete search history.

(56) References Cited

U.S. PATENT DOCUMENTS

| 4,529,400 | A | 7/1985 | Scholten |
|---|---|---|---|
| 4,886,067 | A | 12/1989 | Palermo |
| 4,997,419 | A | 3/1991 | Lakatos et al. |
| 5,441,483 | A | 8/1995 | Avitall |
| 5,500,012 | A | 3/1996 | Brucker et al. |
| 5,743,880 | A | 4/1998 | Hlavka |
| 6,068,621 | A | 5/2000 | Balceta et al. |
| 7,608,056 | B2 | 10/2009 | Kennedy, II |
| 7,682,319 | B2 | 3/2010 | Martin et al. |
| 7,811,277 | B2 | 10/2010 | Boulais |
| 2003/0163085 | A1 | 8/2003 | Tanner et al. |

(Continued)

*Primary Examiner* — Scott T Luan (57) ABSTRACT

A surgical instrument includes a selectively rotatable housing, an adaptor, and a shaft including an end effector. The adaptor is coupled to the housing and is selectively movable between a first position and a second position. The shaft is coupled to one or both of the housing and the adaptor. The end effector is articulable in response to the selective rotation of the housing. The end effector is articulable toward a first direction when the adaptor is positioned in the first position and articulable toward a second direction when the adaptor is positioned in the second position. The first and second directions are different.

9 Claims, 9 Drawing Sheets

(56) References Cited

U.S. PATENT DOCUMENTS

| | | |
|---|---|---|
| 2008/0281293 A1 | 11/2008 | Peh et al. |
| 2009/0043299 A1 | 2/2009 | Racz |
| 2009/0192495 A1 | 7/2009 | Ostrovsky et al. |
| 2009/0270676 A1 | 10/2009 | Sicvol |
| 2009/0312605 A1* | 12/2009 | Hallbeck ................ A61B 17/29 600/131 |
| 2009/0312696 A1 | 12/2009 | Copa et al. |
| 2010/0004591 A1 | 1/2010 | Barenboym et al. |
| 2010/0081863 A1 | 4/2010 | Hess et al. |
| 2010/0121147 A1 | 5/2010 | Oskin et al. |
| 2010/0185161 A1 | 7/2010 | Pellegrino et al. |
| 2013/0197556 A1 | 8/2013 | Shelton, IV et al. |

* cited by examiner

SURGICAL INSTRUMENT WITH ADAPTER FOR FACILITATING MULTI-DIRECTION END EFFECTOR ARTICULATION

CROSS-REFERENCE TO RELATED APPLICATIONS

This application is a continuation of U.S. patent application Ser. No. 13/479,654 filed May 24, 2012, which claims the benefit of and priority to U.S. Provisional Patent Application No. 61/501,478, filed Jun. 27, 2011, the entire disclosure of which is incorporated by reference herein.

BACKGROUND

1. Technical Field

The present disclosure relates generally to surgical instruments for use during a minimally invasive surgical procedure. More particularly, the present disclosure relates to surgical instruments having articulating assemblies that enable multi-direction articulation of end effectors of the surgical instruments.

2. Description of Related Art

Increasingly, many surgical procedures are performed through small openings in the skin. As compared to the larger openings typically required in traditional procedures, smaller openings result in less trauma to the patient. By reducing the trauma to the patient, the time required for recovery is also reduced. Generally, the surgical procedures that are performed through small openings in the skin are referred to as endoscopic. If the procedure is performed on the patient's abdomen, the procedure is referred to as laparoscopic. Throughout the present disclosure, the term minimally invasive is to be understood as encompassing both endoscopic and laparoscopic procedures.

During a typical minimally invasive procedure, surgical objects, such as surgical access devices (e.g., trocar and cannula assemblies) or endoscopes, are inserted into the patient's body through the opening in tissue. In general, prior to the introduction of the surgical object into the patient's body, insufflation gas is used to enlarge the area surrounding the target surgical site to create a larger, more accessible work area. Accordingly, the maintenance of a substantially fluid-tight seal is desirable to inhibit the escape of the insufflation gas and the deflation or collapse of an enlarged surgical site. In response to this, various access devices with sealing features are used during the course of minimally invasive procedures to provide an access for surgical objects to enter the patient's body. Some of these devices are configured for use through a single opening or a naturally occurring orifice (i.e., mouth, anus, or vagina) while allowing multiple instruments to be inserted through the device to access the working space beyond the device.

During procedures employing surgical instruments through a single opening access device, it is advantageous to be able to reposition the end effectors of these surgical instruments in order to achieve desirable orientations of the end effectors within an underlying tissue site. In this regard, a continuing need exists for improved articulating surgical instruments for use through single opening access devices.

SUMMARY

The present disclosure relates to a surgical instrument including a selectively rotatable housing, an adaptor, a drive assembly, and a shaft. The shaft may be coupled to one or both of the housing and the adaptor. The shaft has an end effector.

The housing rotates in a first rotational direction. The first rotational direction may be in the same general direction as one of a first and a second direction of articulation of the end effector of the shaft. The housing includes a body and a seat extending from the body. The seat may define a pair of apertures. The seat may define a groove, or a plurality of grooves, in an external surface of the seat. Each groove defines a track extending between a pair of walls. Each wall of the pair of walls limits movement of one or more projections of the adaptor beyond the respective wall to facilitate the positioning of the adaptor between first and second positions. The track may be at least partially sloped to enable adjustment of tension in the drive assembly.

The adaptor is coupled to the housing and is selectively movable between the first position and the second position. The adaptor may be coupled to the seat of the housing. As discussed above, the adaptor may include a projection, or a plurality of projections, extending from an internal surface of the adaptor. Each projection is movable along one or more grooves of the seat to facilitate movement of the adaptor between the first and second positions. A surface of each projection of the adaptor moves along the track as the adaptor moves between first and second positions. In embodiments, the adaptor includes a pair of protuberances extending therefrom. The protuberances and the apertures of the seat are selectively engagable with each other to secure the adaptor in one of the first and second positions.

The drive assembly is coupled to the end effector and the housing. The drive assembly is movable between first and second orientations. The drive assembly may include two or more cables. The two or more cables may be crossed in one of the first orientation and the second orientation. The two or more cables may be uncrossed in the other of the first orientation and the second orientation.

The end effector is articulable in response to the selective rotation of the housing. The end effector is articulable toward the first direction when the adaptor is positioned in the first position and articulable toward the second direction when the adaptor is positioned in the second position. The first and second directions are different and may be directly opposite one another. The end effector is articulable in the first direction when the drive assembly is positioned in the first orientation and is articulable in the second direction when the drive assembly is positioned in the second orientation.

In embodiments, the shaft may be keyed to one or both of the seat and the adaptor. In embodiments, one of the adaptor and the seat define a channel therein. The other of the adaptor and the seat includes a pin. The pin may be spring actuated. The pin is movable along the channel to facilitate movement of the adaptor between the first and second positions. The channel may include a first bore and a second bore. The first bore may be disposed at a first end of the channel. The second bore may be disposed at a second end of the channel. The first and second bores are selectively engagable with the pin to maintain the adaptor within one of the first and second positions. In embodiments, the adaptor may include a textured outer surface. Rotation of the adaptor may rotate one or both of the shaft and the end effector. In embodiments, the adaptor may include one or more wings extending therefrom that facilitate the rotational movement of the adaptor between the first and second positions.

According to one aspect, a surgical instrument includes a housing, one or more cables and an adaptor. The housing has a shaft extending therefrom. The shaft defines a longitudinal axis and has an end effector secured to a distal end of the shaft. The two or more cables are coupled to the housing and the end effector. The two or more cables impart movement to the end effector in response to movement of the housing. The adaptor is coupled to the shaft and is selectively movable between first and second positions to modify the movement of the end effector by reorienting the relative positions of the two or more cables between a straightened position and a crossed position. When the two or more cables are in the straightened position, the end effector articulates away from the longitudinal axis of the shaft in a first direction. When the two or more cables are in a crossed position, the end effector articulates away from the longitudinal axis of the shaft in a second direction.

In use, the housing rotates in a first rotational direction such that only one of the first and second directions is in the same general direction as the first rotational direction and the other of the first and second directions is in the opposite general direction of the first rotational direction. More particularly, rotation of the housing articulates the end effector relative to the longitudinal axis of the shaft by rotating the two or more cables. A trigger coupled to the housing imparts longitudinal movement to one or more of the two or more cables to operate the end effector. In embodiments, the adaptor may rotate, at most, 180 degrees between the first and second positions.

According to another aspect, a surgical instrument includes a housing and an adaptor. The housing has a shaft defining a longitudinal axis. The shaft has an end effector at a distal end of the shaft. The adaptor is coupled to the housing. The selective movement of the adaptor moves the shaft between first and second positions to enable selective articulation of the end effector relative to the longitudinal axis. When the adaptor is positioned in the first position, the end effector articulates in a first direction. When the adaptor is positioned in the second position, the end effector articulates in a second direction different from the first direction. The end effector articulates in one of the first or second directions relative to the longitudinal axis in response to rotational movement of the housing.

BRIEF DESCRIPTION OF DRAWINGS

Various embodiments of the presently disclosed device are disclosed herein with reference to the drawings, wherein.

DETAILED DESCRIPTION OF EMBODIMENTS

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As shown in the drawings and as described throughout the following description, and as is traditional when referring to relative positioning on an object, the term "proximal" refers to the end of the device that is closer to the user and the term "distal" refers to the end of the device that is farther from the user. In the following description, well-known functions or constructions are not described in detail to avoid obscuring the present disclosure in unnecessary detail.

Figure 1:
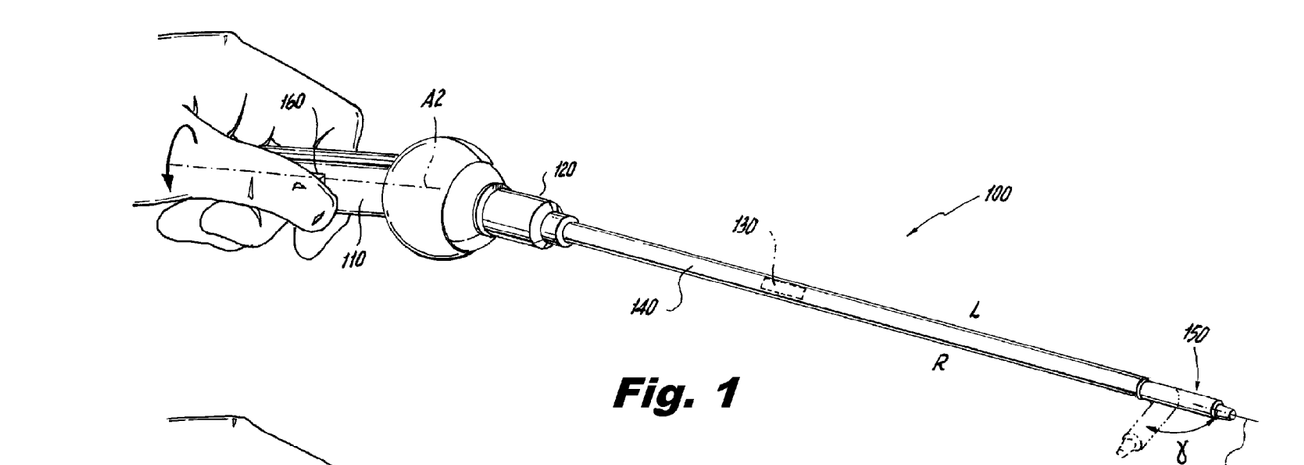
FIG. 1 is a perspective view of one embodiment of a surgical instrument shown in a first configuration in accordance with the present disclosure.
Figure 2:
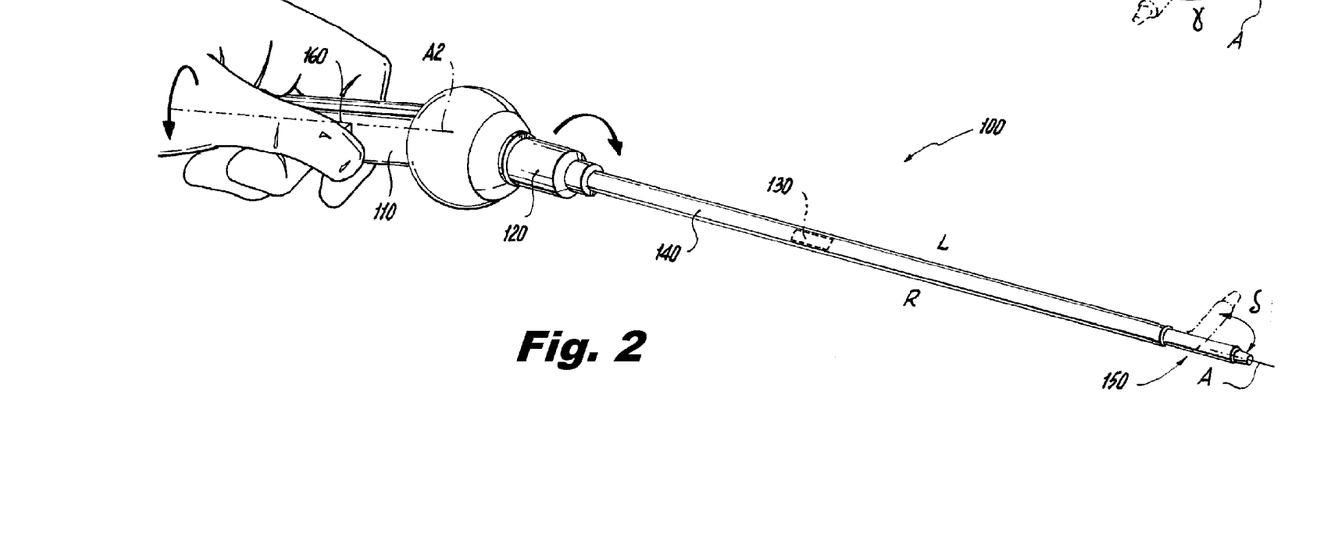
FIG. 2 is a perspective of the surgical instrument of FIG. 1 shown in a second configuration.

Referring initially to FIGS. 1 and 2, the present disclosure is directed to a surgical instrument which is generally referred to as 100. Surgical instrument 100 includes a selectively rotatable housing 110, an adaptor 120, a drive assembly 130, a shaft 140, an end effector 150, and a trigger assembly 160. As depicted in FIGS. 1 and 2, the housing 110 is rotatable (e.g., via wrist rotation of a user) in either a clockwise or counterclockwise direction to articulate the end effector 150 relative to a longitudinal axis "A" extending through the shaft 140 since the end effector 150 is articulably secured to a distal end of the shaft 140. In this regard, the end effector 150 is articulable in response to the selective rotation of the housing 110 about a longitudinal axis "A2" defined through the housing 110. The housing 110 may be configured to rotate in a rotational direction that is either clockwise, counterclockwise, and/or both clockwise and counterclockwise. The adaptor 120, which is coupled to one or both of the housing 110 and the shaft 140, is selectively rotatable between first and second positions (rotating one or both of the shaft 140 and the end effector 150) to change the direction of articulation of the end effector 150 relative to the longitudinal axis "A", which will be discussed in greater detail below.

As illustrated in FIG. 1, the adaptor 120 is positioned in the first position such that the end effector 150 articulates through an angle γ between a first longitudinal position (not shown in phantom) and first articulated position (shown in phantom) in response to the rotation of the housing 110 (FIG. 1 illustrates clockwise rotation of the housing 110). As can be appreciated, the housing 110 can be configured so that counterclockwise rotation articulates the end effector towards the longitudinal axis "A" and clockwise rotation of the housing 110 articulates the end effector 150 away from the longitudinal axis "A" (and vice versa). In the illustrated configuration of FIG. 1, i) the direction of articulation of the end effector 150 away from the longitudinal axis "A" (towards the first articulated position) and ii) the direction of rotation of the housing 110 corresponding to the articulation of the end effector 10 away from the longitudinal axis "A" are directed in the same general direction, (e.g., generally towards the right side "R" of the surgical instrument 100). The surgical instrument 100 can also be configured so that counterclockwise rotation of the housing 110 correspondingly articulates the end effector 150 away from the longitudinal axis "A." Both of these directions are generally towards the left side "L" of the surgical instrument 100 as the end effector 150 approaches the first articulated position.

Referring now to FIG. 2, the adaptor 120 is shown being rotated counterclockwise from the first position into the second position such that the end effector 150 articulates through an angle δ between the first longitudinal position (not shown in phantom) and second articulated position (shown in phantom) in response to the rotation of the housing 110 (FIG. 2 illustrates clockwise rotation of the housing 110). In this configuration, i) the direction of articulation of the end effector 150 away from the longitudinal axis "A" (towards the second articulated position) and ii) the direction of the rotation of the housing 110 corresponding to the articulation of the end effector 150 away from the longitudinal axis "A" are directed in opposite general directions, (e.g., the rotation of the housing 110 is generally towards the right side "R" of the surgical instrument 100 and the articulation of the end effector 150 is away from the longitudinal axis "A" and generally towards the left side "L" of the surgical instrument 100). As can be appreciated, the surgical instrument 100 can also be configured so that the counterclockwise rotation of the housing 110 articulates the end effector 150 generally towards the right side "R" of the surgical instrument 100.

Indeed, the surgical instrument 100 can be configured in any suitable arrangement so that the end effector 150 can articulate through any suitable angle relative to the longitudinal axis "A" in response to rotational movement of the housing 110, not just leftward or rightward. For example, the end effector 150 can be configured to articulate in response to rotation (clockwise or counterclockwise) of the housing 110 between upward and downward or between opposing oblique angles, the direction of articulation being similarly controlled by the positioning of the adaptor 120 between first and second positions. In this regard, the end effector 150 is articulable toward the first direction when the adaptor 120 is positioned in the first position and articulable toward the second direction when the adaptor 120 is positioned in the second position. The first and second directions may be opposite one another, or merely different.

Figure 3:
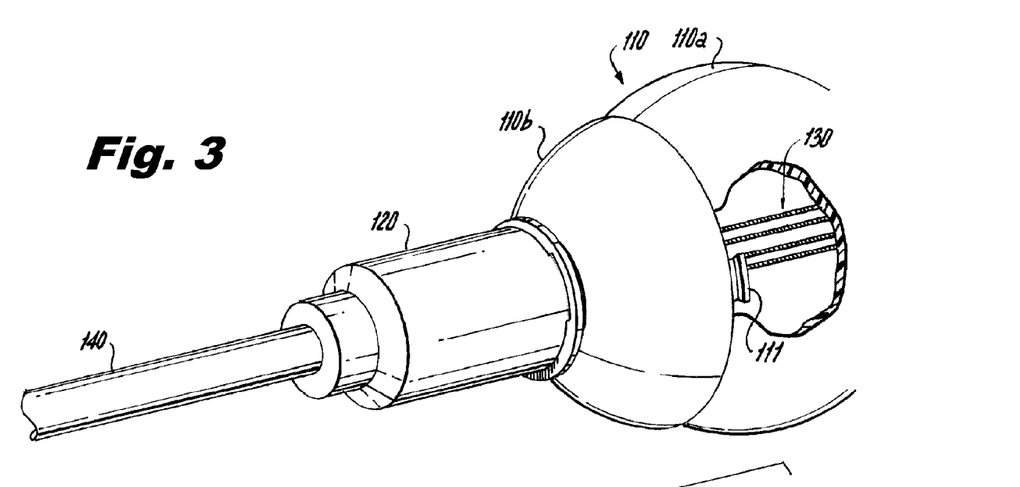
FIG. 3 is an enlarged perspective view of a portion of the presently disclosed surgical instrument shown in FIGS. 1 and 2 with a housing of the surgical instrument having a section removed for clarity.

As best illustrated in FIG. 3, the housing 110 includes a body 110a and a seat 110b extending from the body 110a. The seat 110b is disposed on a distal end of the body 110a and is securable to the body 110a by any suitable structure known in the art (e.g., one or more of any suitable mechanical fastener, adhesive, keyed feature, etc.) Indeed, as illustrated in FIGS. 3 and 4, the body 110a and seat 110b may be secured to one another via any suitable interlocking feature 111 known in the art.

Figures 4, 5, 6:
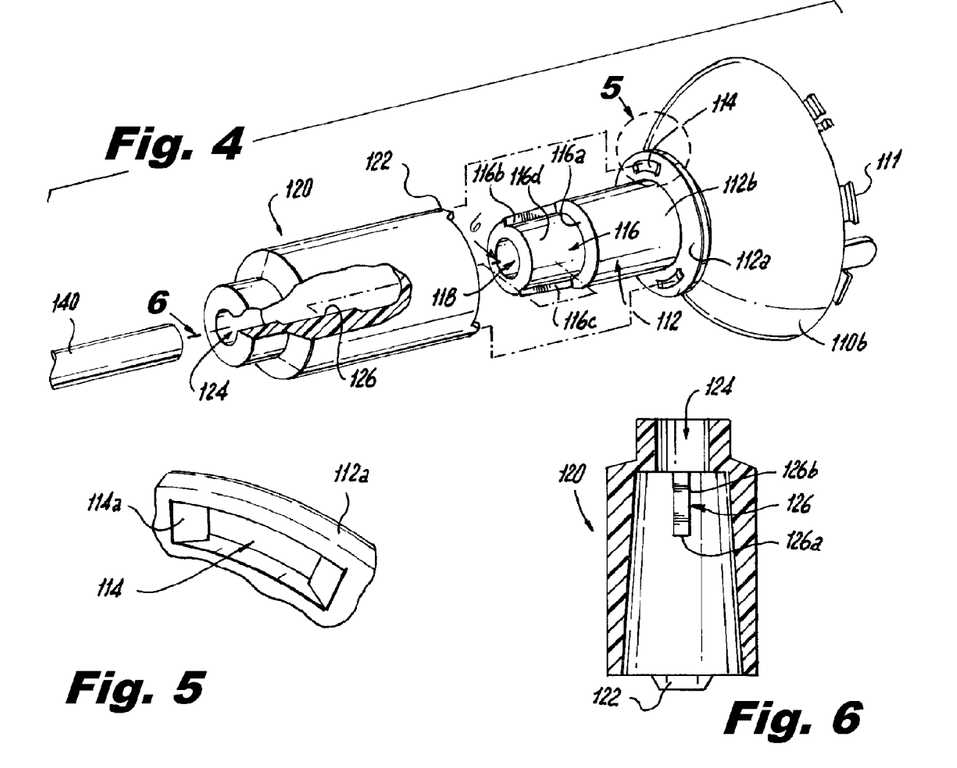
FIG. 4 is an enlarged, exploded, perspective view of a portion of the presently disclosed surgical instrument shown in FIGS. 1 and 2, a section of one embodiment of an adaptor of the presently disclosed surgical instrument having a portion shown in partial cross-section.
FIG. 5 is an enlarged, perspective view of one embodiment of an aperture in accordance with the present disclosure.
FIG. 6 is a cross-sectional view of the adaptor shown in FIG. 4.

With continued reference to FIG. 4, the seat 110b includes a stem 112 having a base 112a and tube 112b. The base 112a may be an annular ring or any other suitable shape. The base 112a defines one or more apertures 114 dimensioned to receive one or more protuberances 122 extending from the adaptor 120. The one or more protuberances 122 may be integrally formed with the adaptor 120 and may be movable between extended and retracted positions to facilitate engagement with the one or more apertures 114. The one or more protuberances 122 will be described in greater detail below. With brief reference to FIG. 5, each aperture 114 includes one or more engaging tabs 114a to facilitate securement of the one or more protuberances 122 within the one or more apertures 114. The tube 112b defines a groove 116 at a distal end and may include a plurality of grooves 116. Each groove 116 may have any suitable shape or dimension to facilitate rotation of the adaptor 120 about the seat 110b. The groove 116 is defined within an external surface of the tube 112b and includes a track 116a, a first wall 116b, and a second wall 116c. The track 116 is defined between the first wall 116b and the second wall 116c. As will be described in greater detail below, the track 116 may be at least partially sloped to enable adjustment of tension in the drive assembly 130. The tube 112b further includes an opening 118 for the reception of a proximal end of the shaft 140. The shaft 140 may be coupled to the housing 110 (e.g., the tube 112b) and/or the adaptor 120 by any suitable means known in the art (e.g., one or more of any suitable mechanical fastener, adhesive, keyed feature, etc.).

FIG. 6 shows a cross-sectional view of the adaptor 120 which includes the one or more protuberances 122 discussed above. Referring now to FIGS. 4 and 6, the one or more protuberances 122 extend from a proximal end of the adaptor 120 for selective engagement with the one or more apertures 114 defined in the base 112a of the stem 112 to secure the adaptor 120 in one of the first and second positions. As depicted in FIG. 4, the adaptor 120 may include a pair of protuberances 122 that alternate engagement with a pair of apertures 114 as the adaptor 120 is moved between first and second positions. The adaptor 120 includes a passage 124 extending therethrough for the reception of at least a portion of the shaft 140 from a distal end of the passage 124 and/or at least a portion of the seat 110b of the housing 110 from a proximal end of the passage 124. As discussed above, the shaft 140 may be coupled to the adaptor 120 (and/or the housing 110) by any suitable means known in the art (e.g., one or more of any suitable mechanical fastener, adhesive, keyed feature, etc.). The passage 124 may be shaped and dimensioned to accommodate the stem 112 of seat 110b. From FIG. 6, one or more projections 126 extend from an internal surface of the adaptor 120. With continued reference to FIGS. 4 and 6, each projection 126 is movable along the one or more grooves 116 defined within the tube 112a of the seat 110b to facilitate movement of the adaptor 120 between the first and second positions. As the adaptor 120 moves between first and second positions, a bottom surface 126a of each projection 126 of the adaptor 120 moves along the track 116a while a front surface 126b of each projection 126 moves along a front surface 116d of the groove 116.

Figure 7:
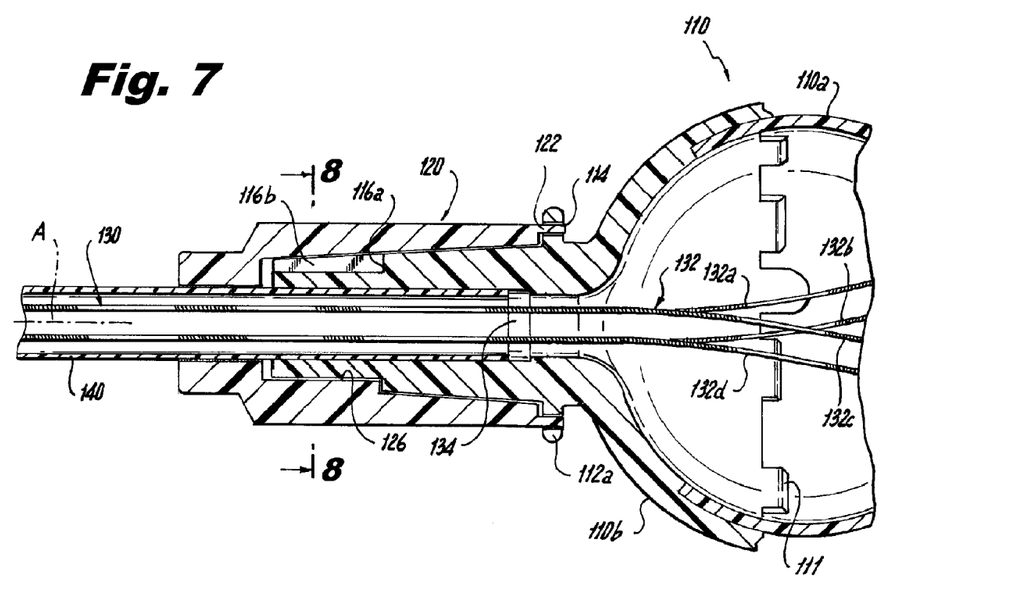
FIG. 7 is an enlarged, cross-sectional view of a portion of the presently disclosed surgical instrument shown in FIGS. 1 and 2 with the adaptor being shown in a first position.
Figure 8:
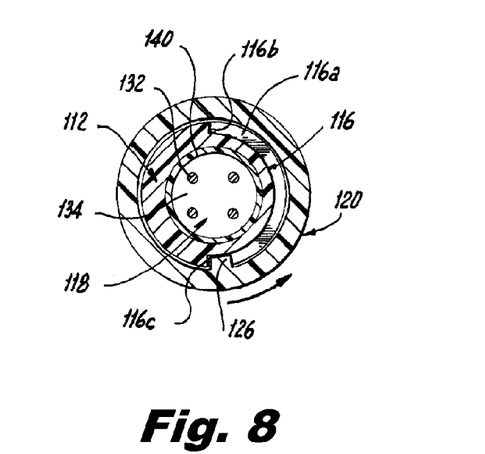
FIG. 8 is a cross-sectional view taken along section line 8-8 of the portion of the presently disclosed surgical instrument shown in FIG. 7.
Figure 9:
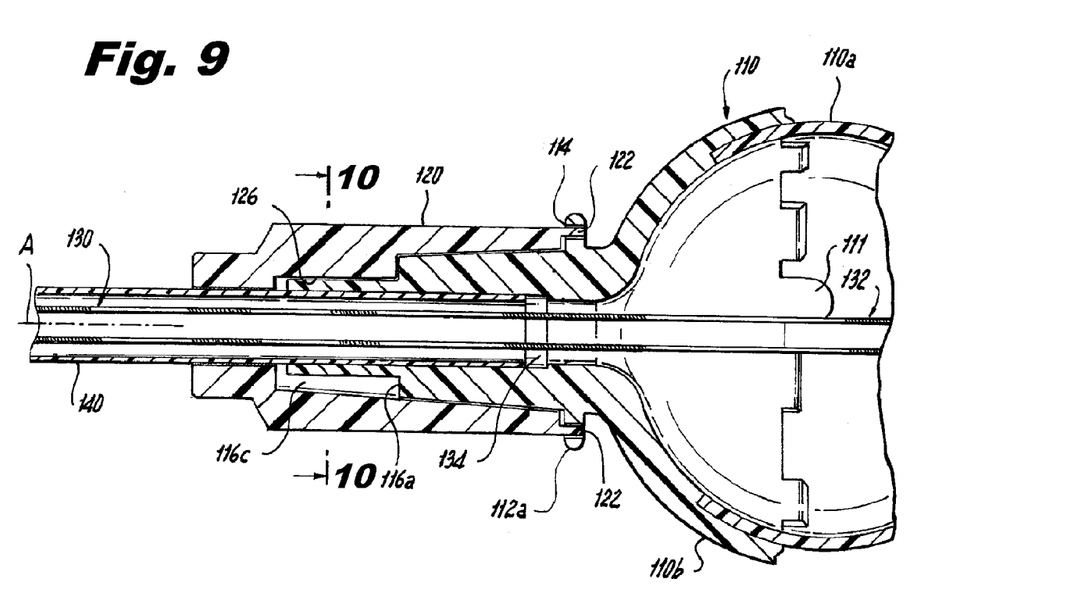
FIG. 9 is an enlarged, cross-sectional view of a portion of the presently disclosed surgical instrument shown in FIGS. 1 and 2 with the adaptor being shown in a second position.
Figure 10:
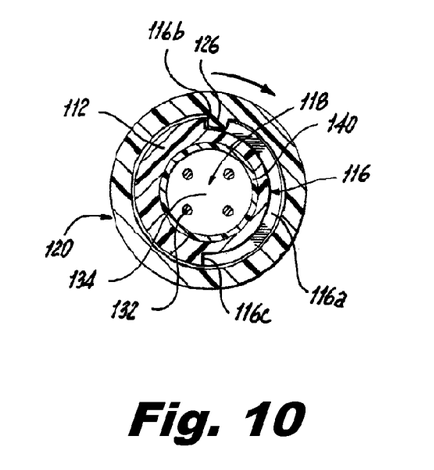
FIG. 10 is a cross-sectional view taken along section line 10-10 of the portion of the presently disclosed surgical instrument shown in FIG. 9.

Turning now to FIGS. 7-10, the adaptor 120, as discussed above, is rotatable between first and second positions to change the direction of articulation of the end effector 150 relative to the longitudinal axis "A." In particular, FIGS. 7-8 depict the adaptor 120 being disposed in a first position, where the projection 126 of the adaptor 120 is disposed abutting wall 116c of groove 116. In contrast, FIGS. 9-10 depict the adaptor 120 being disposed in a second position, where the projection 126 of the adaptor 120 is disposed abutting wall 116b of groove 116. In this manner, each wall 116b, 116c limits movement of the projection 126 beyond the respective wall 116b, 116c to facilitate the positioning of the adaptor 120 between first and second positions.

As best illustrated in FIGS. 7 and 9, drive assembly 130 includes any number of driving members 132 (e.g., cables 132a, 132b, 132c, and 132d) coupled to the end effector 150 and the housing 110 (e.g., coupled to the trigger assembly 160 and/or the body 110a) to effectuate the articulation and/or operation of the end effector 150. In particular, the driving members 132 are used to impart movement to the end effector 150 in response to movement of the housing 110 and/or actuation of the trigger assembly 160. The trigger assembly 160 may be configured to impart longitudinal movement to one or more of the driving members 132 to operate the end effector 150 (e.g., open and close a pair of jaws of the end effector 150). The driving members 132 may be secured to the seat 110 via a mount 134. In one embodiment, the mount 134 may be rotatably positioned within the opening 118 extending through the stem 112. In use, when the adaptor 120 is disposed in the first position (FIGS. 7-8), two or more of the driving members 132 may be positioned in a first orientation (e.g., a crossed configuration) to facilitate the articulation of the end effector 150 in a first direction relative to the longitudinal axis "A" of the shaft 140 (illustrated in FIG. 1). Alternatively, when the adaptor is disposed in the second position (FIGS. 9-10), the driving members 132 are in a second orientation (e.g., straightened or uncrossed configuration) to facilitate the articulation of the end effector 150 in a second direction relative to the longitudinal axis "A" of the shaft 140 (illustrated in FIG. 2). In embodiments, the driving members 132 may be limited to rotating through an angle of at most 180 to prevent undesirable tangling of the drive members 132. As discussed above with respect to FIGS. 1 and 2, the first and second direction can be arranged in any suitable configuration, e.g., up/down directions, opposite oblique directions, etc.

Figures 11, 12, 13:
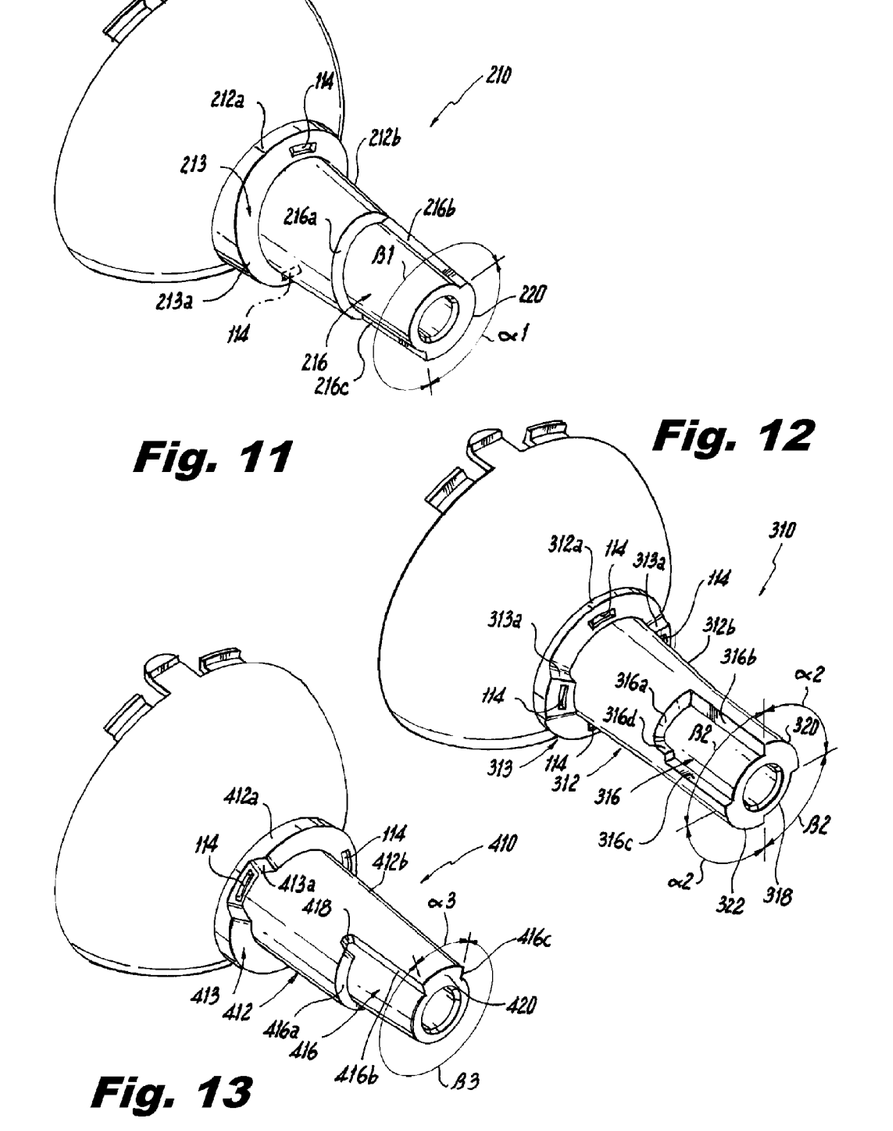
FIG. 11 is a perspective view of one embodiment of a seat of the presently disclosed surgical instrument shown in FIGS. 1 and 2.
FIG. 12 is a perspective view of another embodiment of a seat of the presently disclosed surgical instrument shown in FIGS. 1 and 2.
FIG. 13 is a perspective view of yet another embodiment of a seat of the presently disclosed surgical instrument shown in FIGS. 1 and 2.

Referring now to FIGS. 11-13, alternate embodiments of a seat are illustrated and are described herein only to the extent necessary to describe the differences in construction and operation thereof. FIG. 11 shows one embodiment of a seat generally referred to as 210. Seat 210 includes a stem 212 with a base 212a and a tube 212b. Base 212a includes surface 213 with a slope 213a. As illustrated in FIG. 11, the slope 213a may be disposed at any suitable angle and may spiral along the tube 212b. The slope 213a is arranged to adjust tension in the drive members 132. The surface 213 may also include one or more apertures 114 defined therein. Tube 212b defines a groove 216 and raised portion 220. Groove 216 includes a track 216a, a first wall 216b, and a second wall 216c. Groove 216 is defined along any suitable angle β1 while raised portion 220 is defined along any suitable angle α1. Angles α1 and β1 may be any suitable explementary angles (e.g., 140 degrees and 220 degrees). Track 216a is sloped at any suitable angle to adjust tension in the drive members 132. Track 216a and slope 213a may be arranged commensurate with one another to facilitate the adjustment of tension in the drive members 132. In embodiments, track 216a and/or slope 213a may have a planar, spiral, zig-zag, or any other suitably shaped and/or dimensioned configuration known in the art. As can be appreciated, the adaptor 120 may include a single protuberance 122 for alternating engagement with a pair of apertures 114 defined along surface 213.

FIG. 12 shows another embodiment of a seat generally referred to as 310. Seat 310 includes a stem 312 with a base 312a and a tube 312b. Base 312a includes surface 313 with one or more ramps 313a. The one or more ramps 313a may be disposed at any suitable angle. Each ramp 313a is arranged to adjust tension in the drive members 132. The ramps 313a may also include one or more apertures 114 defined therein. Tube 312b defines first and second grooves 316, 318 and first and second raised portions 320, 322. The first and second grooves 316, 318 each define an angle β2. The first and second raised portions 320, 322 each define an angle α2. α2 may be substantially equal to β2 (e.g., each angle is 90 degrees). In this regard, α2 and β2 may be supplementary angles. First groove 316 includes a track 316a, a first wall 316b, a second wall 316c, and one or more ramps 316d. In this regard, track 316a is sloped (e.g., upwards at one or both of the ends via one or more ramps 316d) to adjust tension in the drive members 132 when the adaptor 120 is disposed in one of the first and second positions. Second groove 318 is substantially identical to first groove 316 but is disposed on a diametrically opposed side of the tube 312b. The one or more ramps 316d in each track 316a and/or the one or more ramps 313a on surface 313 may be the same or different and may be arranged at any suitable orientation to achieve any desirable tension in one or more of the drive members 132 due to various properties and/or dimensions and/or amount of drive members 132 included in one of the presently disclosed embodiments of the presently disclosed surgical instrument. Indeed, the first and second grooves 316, 318 can be arranged with any suitable combination of dimensions, shapes, etc. to enable the adaptor 120 to rotate between first and second positions.

FIG. 13 shows another embodiment of a seat generally referred to as 410. Seat 410 includes a stem 412 with a base 412a and a tube 412b. Base 412a includes surface 413 with one or more notches 413a. The one or more notches 413a may be disposed at any suitable angle. Each notch 413a is arranged to adjust tension in the drive members 132. Each notch 413a may also include one or more apertures 114 defined therein. Tube 412b defines a groove 416 and a raised portion 420. Groove 416 defines an angle β3 and raised portion 420 defines an angle α3. Angles α3 and β3 may be any suitable explementary angles (e.g., 40 degrees and 320 degrees). Groove 416 includes a track 416a, a first wall 416b, a second wall 416c, and one or more notches 418. In this regard, track 416a is sloped (e.g., downwards at one or both of the ends via one or more notches 418) to adjust tension in the drive members 132. Notches 413a and 418 may be the same or different and may be arranged at any suitable orientation to achieve any desirable tension in one or more of the drive members 132 due to various properties and/or dimensions and/or amount of drive members 132 included in one of the presently disclosed embodiments of the presently disclosed surgical instrument.

Figure 14:
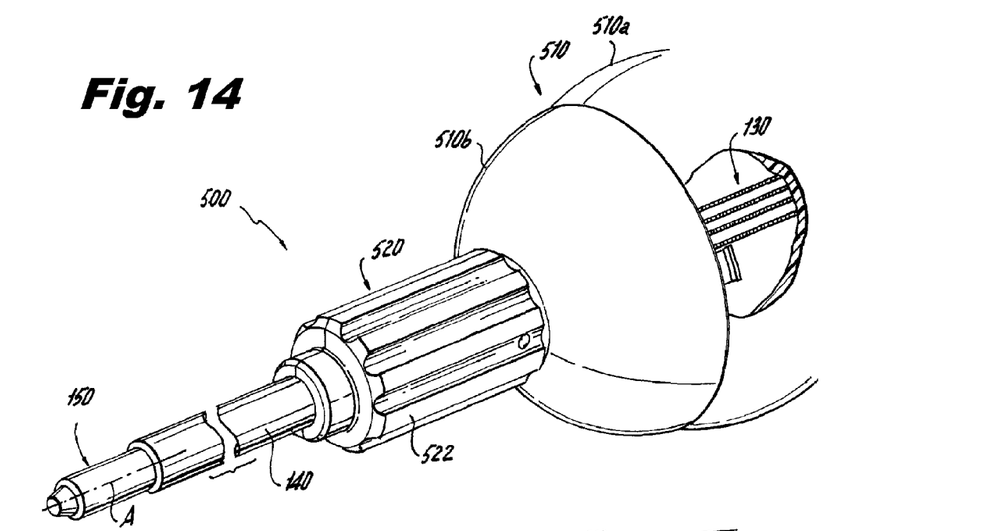
FIG. 14 is a perspective view of a portion of another embodiment of a surgical instrument in accordance with the present disclosure.

With reference now to FIGS. 14-18, an alternate embodiment of a surgical instrument is generally referred to as 500 and is described herein only to the extent necessary to describe the differences in construction and operation thereof. Turning now to FIG. 14, surgical instrument 500 includes a housing 510, an adaptor 520, a drive assembly 130, a shaft 140, and an end effector 150.

Figure 15:
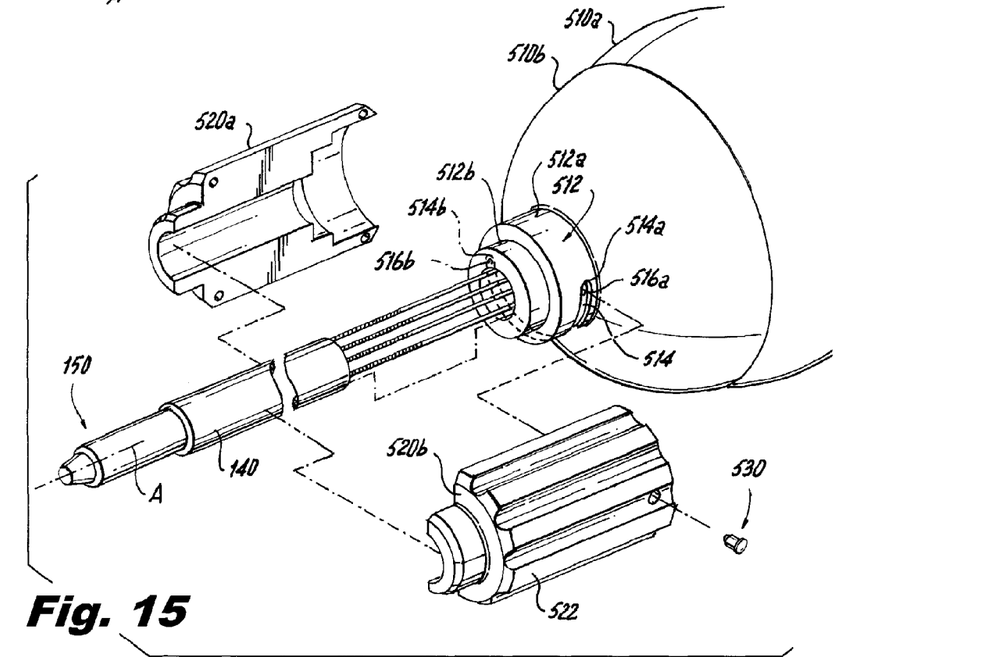
FIG. 15 is an exploded, perspective view of the portion of the surgical instrument shown in FIG. 14.

As best shown in FIG. 15, the housing 510 has a body 510a and a seat 510b extending from the body 510a. The seat 510b includes a stem 512 having a base 512a and a tube 512b extending from the base 512a. The base 512a defines a channel 514 that extends along an external surface of the base 512a. With brief reference to FIGS. 17-18, the channel 514 may be defined such that the ends 514a, 514b of the channel 514 are longitudinal spaced from one another along the longitudinal axis "A" of the shaft 140. In this regard, the channel 514 may have a substantially spiral configuration, although any other suitable configuration is contemplated (e.g., sinusoidal, chevron, linear, zig-zag, etc.). The channel 514 includes a first bore 516a and a second bore 516b defined therein at opposite ends of the channel 514 that are dimensioned to accommodate a pin 530 secured to the adaptor 520. In this respect, the first and second bores 516a, 516b are selectively engagable with the pin 530 to maintain the adaptor 520 within one of the first and second positions. In embodiments, the channel 514 may include any number of bores positioned at various locations along the length of the channel 514 to position the adaptor 520 in any number of positions for orienting the end effector 150 in any desired orientation. In embodiments, the channel 514 may be defined in the adaptor 520 and the base 512a may include a pin 530. The pin 530 and the adaptor 520 will be described in greater detail below.

As illustrated in this embodiment, and best shown in FIG. 15, the adaptor 520 may include a first section 520a and a second section 520b that are secured together, e.g., via interference fit, over at least a portion of shaft 140 and at least a portion of stem 512 of seat 510b. With reference to FIGS. 14 and 15, adaptor 520 includes a textured surface 522 to facilitate gripping. The pin 530 is secured within adaptor 520.

Figure 16:
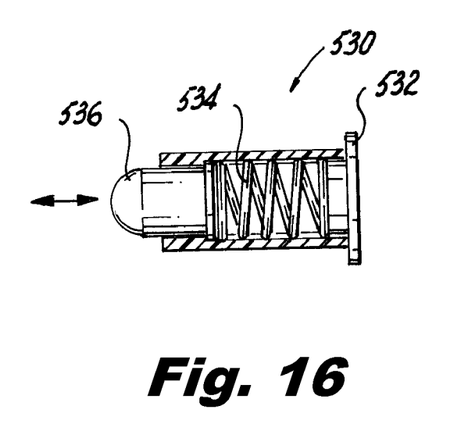
FIG. 16 is an enlarged, partial cross-sectional view of one embodiment of a pin in accordance with the present disclosure.
Figure 17:
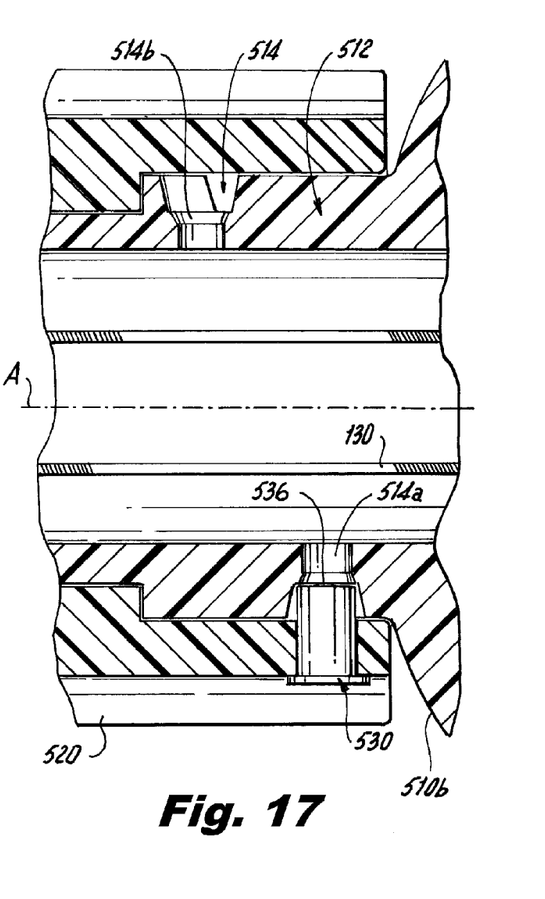
FIGS. 17-18 are enlarged, progressive, partial cross-sectional views of a portion of an embodiment of an adaptor and a portion of an embodiment of a seat illustrating the positioning of the adaptor between first and second positions.

As shown in FIG. 16, pin 530 includes a head 532, a biasing member 534, and a tip 536. The biasing member 534 facilitates movement of the tip 536 (e.g., via spring actuation) between locked and unlocked conditions upon actuation of the head 532. The biasing member 534 may be a spring or any other suitable biasing mechanism known in the art.

Referring again to FIG. 17, the adaptor 520 is in the first position with the pin 530 shown in a retracted position such that the tip 536 is not locked into first bore 514a and adaptor 520 is rotatable toward the second position. When the pin 530 is in an extended position (FIG. 18) the tip 536 of the pin 530 is locked into first bore 514a of channel 514 of stem 512 to maintain the adaptor 520 in the first position. Upon actuation of the pin 530, the biasing member 534 moves the tip 536 into an unlocked condition, e.g., where the tip 536 retracts toward the head 532 to the retracted position and out of engagement with first bore 514a (shown in FIG. 17), so that the pin 530 may travel along the channel 514 upon rotation of the adaptor 520.

Figure 18:
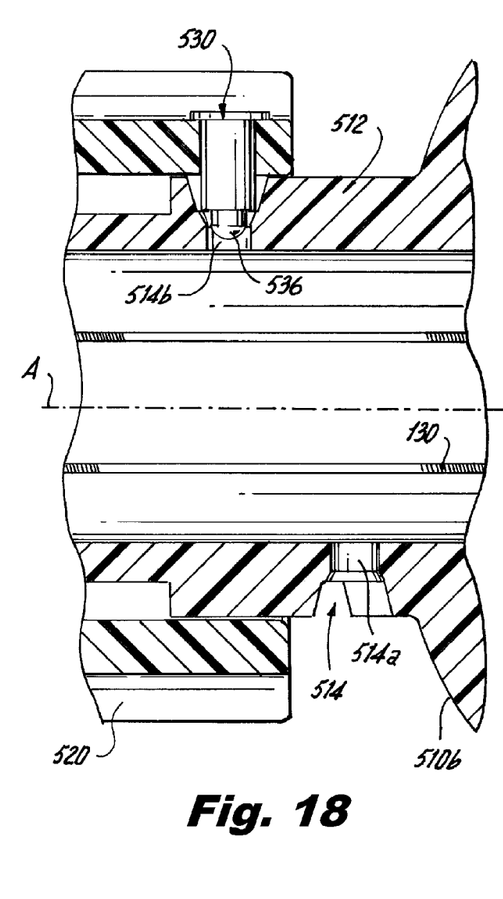

With reference to FIG. 18, when the adaptor 520 is rotated to the other end of the channel 514, the tip 536 of the pin 530 extends into the second bore 514b via the biasing forces of the biasing member 534, locking the tip 536 into the second bore 514b and the adaptor 520 into the second position. As can be appreciated, another actuation of the pin 530 retracts the tip 536 from the second bore 514b so that the adaptor 520 may be selectively repositioned into either the first or the second position as described above. It should be noted that the adaptor 520 may longitudinally translate along the longitudinal axis "A" as the adaptor 520 moves between the first and second positions (see FIGS. 17-18). In particular, where the channel 514 is disposed in a spiral configuration, the pin 530 cams along the channel 514 along a spiral path moving the adaptor 520 axially along the longitudinal axis "A." As discussed above, the channel 514 may be arranged in any suitable configuration (e.g., sinusoidal, chevron, linear, zig-zag, etc.), some of which are configured to axially translate the adaptor 520 along the longitudinal axis "A" and some of which are configured to maintain the adaptor 520 in an axially stationary position. The particular channel 514 may be selected to accommodate the various properties and/or orientations of various drive members (e.g., diameters, spring rates, crossed and uncrossed orientations, etc.) in order to achieve predetermined operations and/or articulations and/or other movements of the end effector 150.

Figure 19:
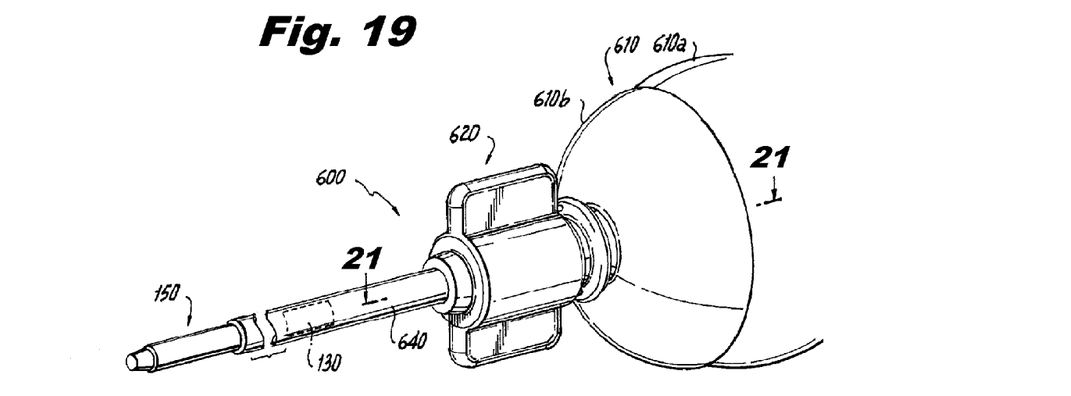
FIG. 19 is a perspective view of a portion of yet another embodiment of a surgical instrument in accordance with the present disclosure.
Figure 20:
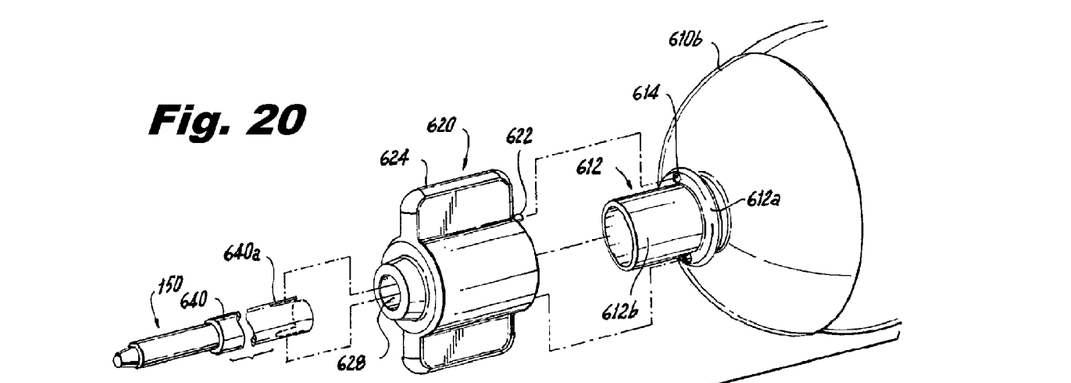
FIG. 20 is an exploded, perspective view of the portion of the presently disclosed surgical instrument illustrated in FIG. 19.
Figure 21:
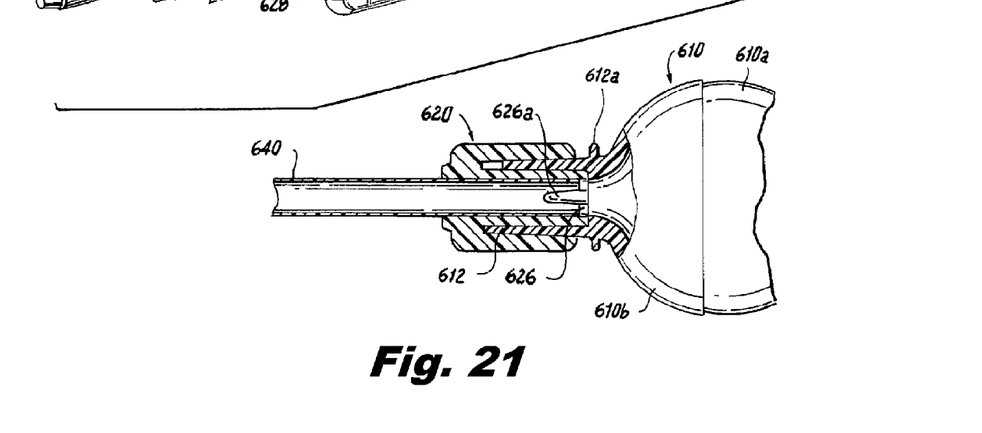
FIG. 21 is a partial cross-sectional view of the portion of the presently disclosed surgical instrument illustrated in FIG. 19.

With reference now to FIGS. 19-21, another embodiment of a surgical instrument is generally referred to as 600 and is described herein only to the extent necessary to describe the differences in construction and operation thereof. Surgical instrument 600 includes a housing 610, an adaptor 620, a drive assembly 130, a shaft 640, and an end effector 150.

The housing 610 has a body 610a and a seat 610b extending from the body 610a. As best shown in FIG. 20, the seat 610b includes a stem 612 having a base 612a and a tube 612b extending from the base 612a. The base 612a may be an annular ring or any other suitable shape. The base 612a defines one or more apertures 614 dimensioned to receive one or more protuberances 622 extending from the adaptor 622.

The adaptor 620 includes one or more wings 624 extending therefrom for facilitating gripping of the adaptor 620 and the rotational movement of the adaptor 620 between first and second positions. When the adaptor 620 is positioned in one of the first and second positions, the one or more protuberances 622 engage the one or more apertures 614 defined within the base 612a of the stem 612 to maintain the adaptor 620 secured in the respective first or second position. The one or more protuberances 622 may be movable between extended and retracted positions. In particular, the adaptor 620 may be axially movable, (e.g., retracted proximally and/or extended distally) to actuate the one or more protuberances 622 between extended and retracted positions for enabling the one or more protuberances 622 to be selectively positioned within the one or more apertures 614. In this respect, when positioned within the one or more apertures 614 (e.g., in an extended position), the one or more protuberances 622 maintain the adaptor 620 in one of the first and second positions. In comparison, when the one or more protuberances 622 are spaced from the one or more apertures 614 (e.g., in a retracted position), the adaptor 620 is rotatable between the first and second positions. The one or more protuberances 622 may include any suitable biasing mechanism (e.g., a spring) for enabling the one or more protuberances 622 to move between extended and retracted positions.

Referring now to FIGS. 20-21, adaptor 620 includes an opening 628 for the reception of shaft 640. The shaft 640 may be keyed to the seat 610b (e.g., via stem 612) and/or the adaptor 620. For example, as shown in FIG. 21, the adaptor 620 includes a mounting member 626 with one or more mounting arms 626a extending therefrom. As best shown in FIG. 20, the shaft 640 defines one or more mounting features 640a that are configured to engage the mounting arms 626a of the mounting member 626 when the shaft 640 is secured to the adaptor 620. When engaged, the mounting arms 626a of the mounting member 626 rotate the shaft 640 via the mounting features 640a when the adaptor 620 is moved between first and second positions.

It will be understood that various modifications may be made to the embodiments of the presently disclosed device. Therefore, the above description should not be construed as limiting, but merely as exemplifications of embodiments. Those skilled in the art will envision other modifications within the scope and spirit of the present disclosure.

What is claimed is:

1. A surgical instrument, comprising:
a selectively rotatable housing;
an adaptor coupled to the housing, the adaptor being selectively movable between a first position and a second position with respect to the housing;
a shaft having an end effector, the shaft being coupled to at least one of the housing or the adaptor and keyed to at least one of the housing or the adaptor, the end effector being articulable in response to selective rotation of the housing, the end effector being articulable in a first direction when the adaptor is positioned in the first position and articulable in a second direction when the adaptor is positioned in the second position, the first and second directions being different; and
a drive assembly coupled to the end effector and the housing, the drive assembly including at least two cables, the at least two cables being crossed in one of a first orientation of the drive assembly or a second orientation of the drive assembly, and being uncrossed in the other of the first orientation or the second orientation.

2. The surgical instrument of claim 1, wherein the end effector is articulable in the first direction when the drive assembly is positioned in the first orientation and articulable in the second direction when the drive assembly in positioned in the second orientation.

3. The surgical instrument of claim 1, further comprising a trigger assembly coupled to the drive assembly, the trigger assembly configured to impart longitudinal movement to the drive assembly to operate the end effector.

4. The surgical instrument of claim 1, wherein one of the adaptor or the housing defines a channel therein, the other of the adaptor and the housing includes a pin, the pin being movable along the channel to facilitate movement of the adaptor between the first and second positions.

5. The surgical instrument of claim 4, wherein the channel includes a first bore disposed at a first end of the channel and a second bore disposed at a second end of the channel, the pin selectively engagable with the first and second bores such that the adaptor is maintained in one of the first or second positions.

6. The surgical instrument of claim 5, wherein the pin includes a head, a tip, and a biasing member, the biasing member configured to urge the tip into and out of engagement with the first or second bores upon actuation of the head.

7. The surgical instrument of claim 1, wherein the adaptor includes at least one wing extending therefrom, the at least one wing configured to facilitate rotational movement of the adaptor between the first and second positions.

8. The surgical instrument of claim 1, wherein the housing includes a body and a seat and the adaptor includes a cavity and a projection extending from an internal surface thereof, the cavity of the adaptor configured to receive the body of the housing.

9. The surgical instrument of claim 8, wherein the seat defines a groove in an external surface thereof, the projection configured to move along the groove to facilitate movement of the adaptor between the first and second positions.

* * * * *